United States Patent
Bang et al.

(10) Patent No.: US 11,986,803 B2
(45) Date of Patent: May 21, 2024

(54) PARTIAL OXIDATION PROCESS OF HYDROCARBONS

(71) Applicants: LG CHEM, LTD., Seoul (KR); SEOUL NATIONAL UNIVERSITY R&DB FOUNDATION, Seoul (KR)

(72) Inventors: Jungup Bang, Daejeon (KR); Do Heui Kim, Seoul (KR); Gyo Hyun Hwang, Daejeon (KR); Jongwook Jung, Daejeon (KR); Yongju Bang, Daejeon (KR); Youngseok Ryou, Daejeon (KR); Jeongeun Kim, Gunpo-si (KR)

(73) Assignees: LG CHEM, LTD., Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 606 days.

(21) Appl. No.: 16/978,901

(22) PCT Filed: Mar. 13, 2019

(86) PCT No.: PCT/KR2019/002893
§ 371 (c)(1),
(2) Date: Sep. 8, 2020

(87) PCT Pub. No.: WO2019/177362
PCT Pub. Date: Sep. 19, 2019

(65) Prior Publication Data
US 2021/0046458 A1    Feb. 18, 2021

(30) Foreign Application Priority Data
Mar. 13, 2018   (KR) .................. 10-2018-0029319

(51) Int. Cl.
*B01J 23/63*    (2006.01)
*B01J 23/10*    (2006.01)
(Continued)

(52) U.S. Cl.
CPC ............... *B01J 23/63* (2013.01); *B01J 23/10* (2013.01); *B01J 35/40* (2024.01); *B01J 35/615* (2024.01);
(Continued)

(58) Field of Classification Search
CPC . B01J 23/63; B01J 23/10; B01J 35/023; B01J 35/1019; C01B 3/40;
(Continued)

(56) References Cited

U.S. PATENT DOCUMENTS 3,436,358 A    4/1969  Thygensen
5,334,789 A    8/1994  Komatsu et al.
(Continued)

FOREIGN PATENT DOCUMENTS

CA    1116587 A    1/1982
CN    102344339 A  2/2012
(Continued)

OTHER PUBLICATIONS

International Search Report issued in PCT/KR2019/002893 (PCT/ISA/210), dated Jun. 17, 2019.
(Continued)

*Primary Examiner* — Coris Fung
*Assistant Examiner* — Keling Zhang
(74) *Attorney, Agent, or Firm* — Birch, Stewart, Kolasch & Birch, LLP

(57) ABSTRACT

A partial oxidation process of hydrocarbons is provided, including bringing an inlet gas into contact with a catalyst, the inlet gas including a hydrocarbon raw material gas and a hydrogen chloride gas, wherein the catalyst includes a catalyst material including palladium (Pd), which catalyst material is supported on a carrier including cerium oxide
(Continued)

(CeO$_2$) and an amount of catalyst material supported on the carrier is 2 wt % to 10 wt % based on a total weight of the catalyst.

13 Claims, 7 Drawing Sheets

(51) Int. Cl.
  *B01J 35/40* (2024.01)
  *B01J 35/61* (2024.01)
  *C01B 3/40* (2006.01)
(52) U.S. Cl.
  CPC ........ *C01B 3/40* (2013.01); *C01B 2203/0261* (2013.01); *C01B 2203/1064* (2013.01); *C01B 2203/1082* (2013.01)
(58) Field of Classification Search
  CPC .... C01B 2203/0261; C01B 2203/1064; C01B 2203/1082
  USPC ....................................................... 252/373
  See application file for complete search history.

(56) References Cited

U.S. PATENT DOCUMENTS

| | | |
|---|---|---|
| 6,506,705 B2 | 1/2003 | Blanchard et al. |
| 7,364,712 B2 | 4/2008 | Ohtsuka et al. |
| 7,767,617 B2 | 8/2010 | Larcher et al. |
| 8,216,960 B2 | 7/2012 | Orsenigo et al. |
| 2006/0058184 A1 | 3/2006 | Jiang et al. |
| 2007/0041895 A1 | 2/2007 | Fukunaga |

FOREIGN PATENT DOCUMENTS

| | | |
|---|---|---|
| CN | 103301836 A | 9/2013 |
| CN | 103920507 A | 7/2014 |
| GB | 1016094 A | 1/1966 |
| GB | 1118939 A | 7/1968 |
| JP | 6-9445 A | 1/1994 |
| JP | 2003-326166 A | 11/2003 |
| KR | 10-2000-0057428 A | 9/2000 |
| KR | 10-2003-0061395 A | 7/2003 |
| KR | 10-2005-0106106 A | 11/2005 |
| KR | 10-2008-0037900 A | 5/2008 |
| KR | 10-2010-0074017 A | 7/2010 |
| WO | WO 02/40152 A1 | 5/2002 |
| WO | WO2017/216653 | * 12/2017 |

OTHER PUBLICATIONS

Scharfe et al., "Mechanism of Ethylene Oxychlorination on Ceria", ACS Catalysis, vol. 8, 2018, pp. 2651-2663.

Zichittella et al., "Catalytic Oxychlorination versus Oxybromination for Methane Functionalization", ACS Catalysis, vol. 7, 2017, pp. 1805-1817.

* cited by examiner

[Figure 1]
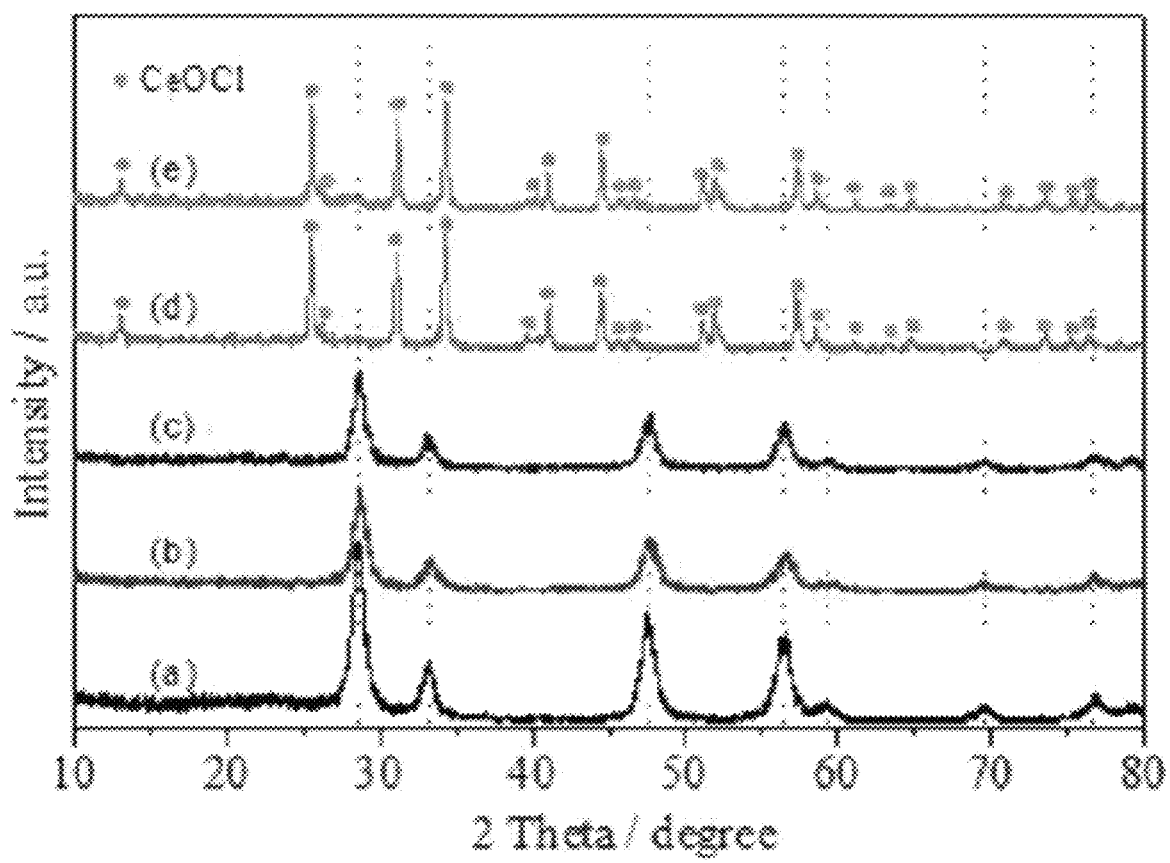

[Figure 2]
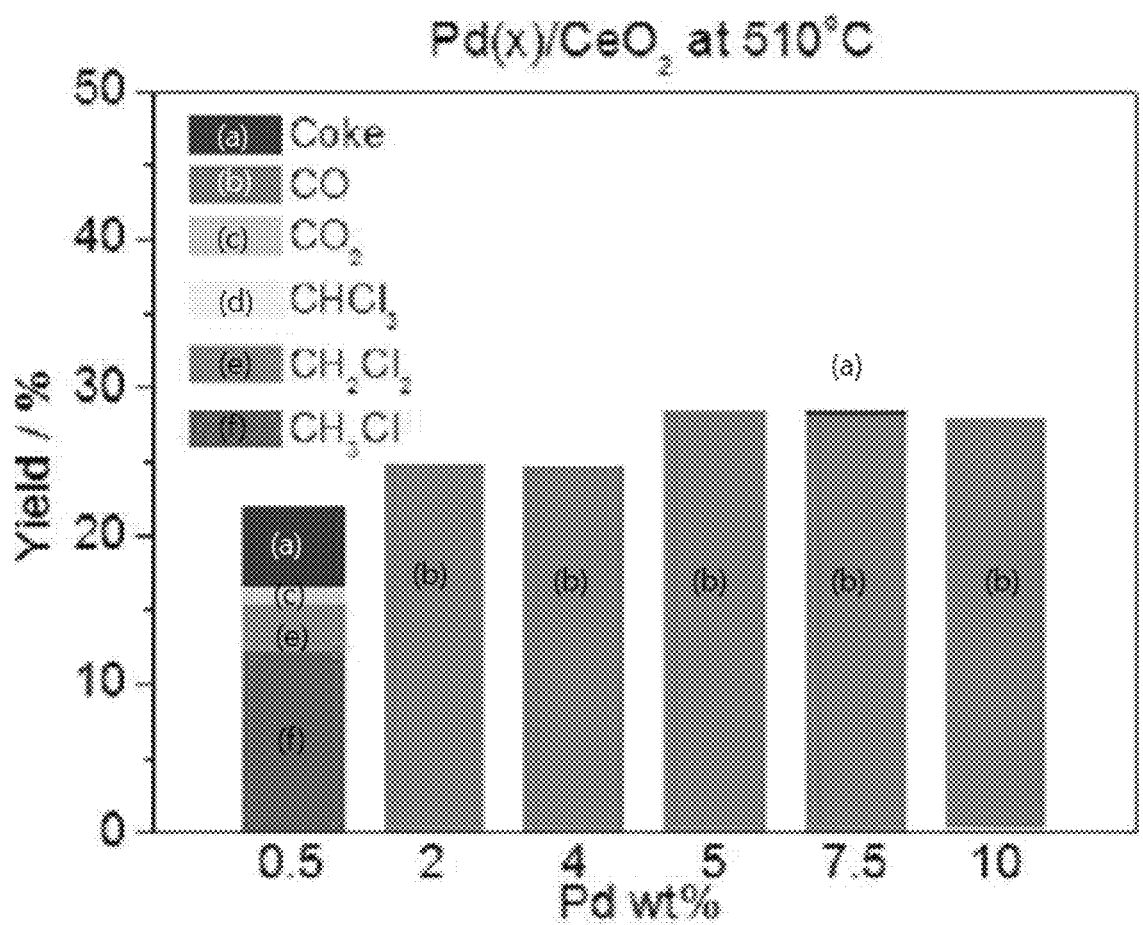

[Figure 3]
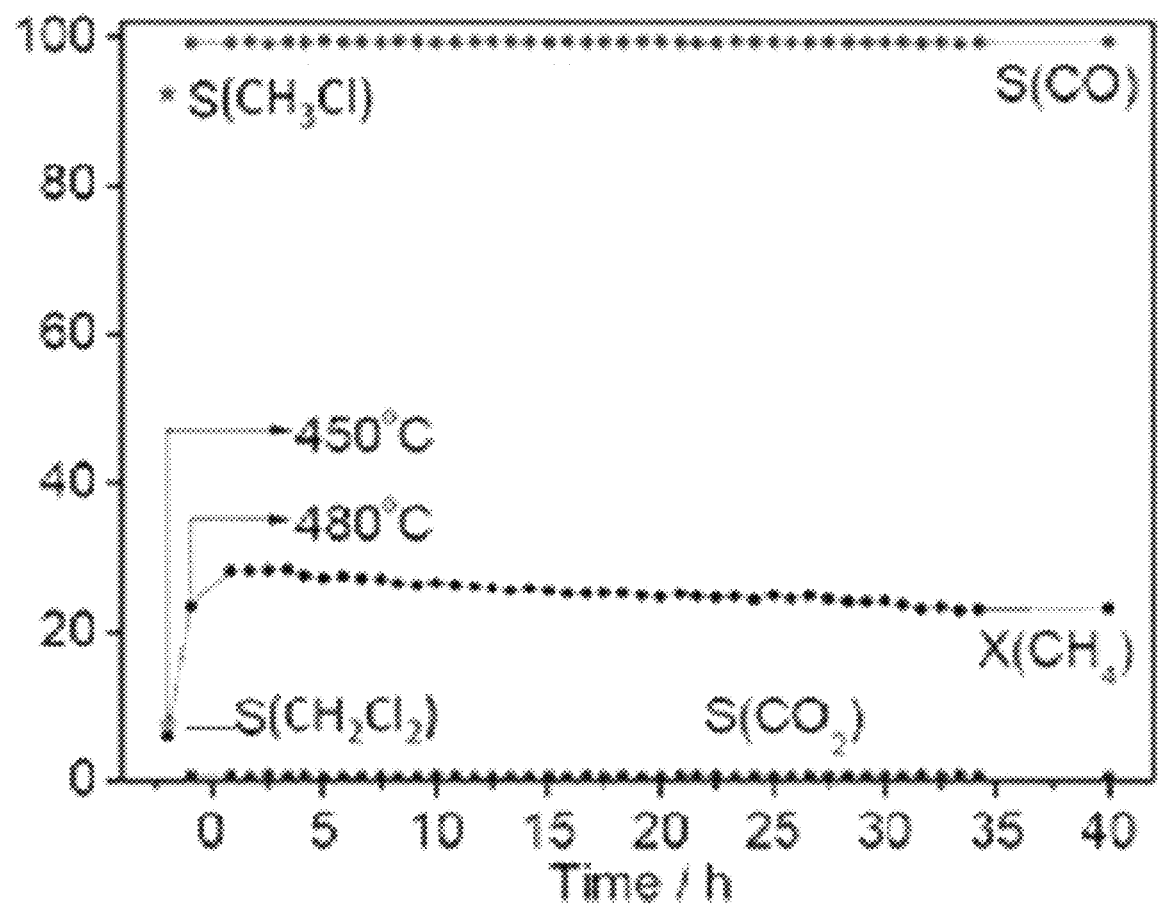

[Figure 4]
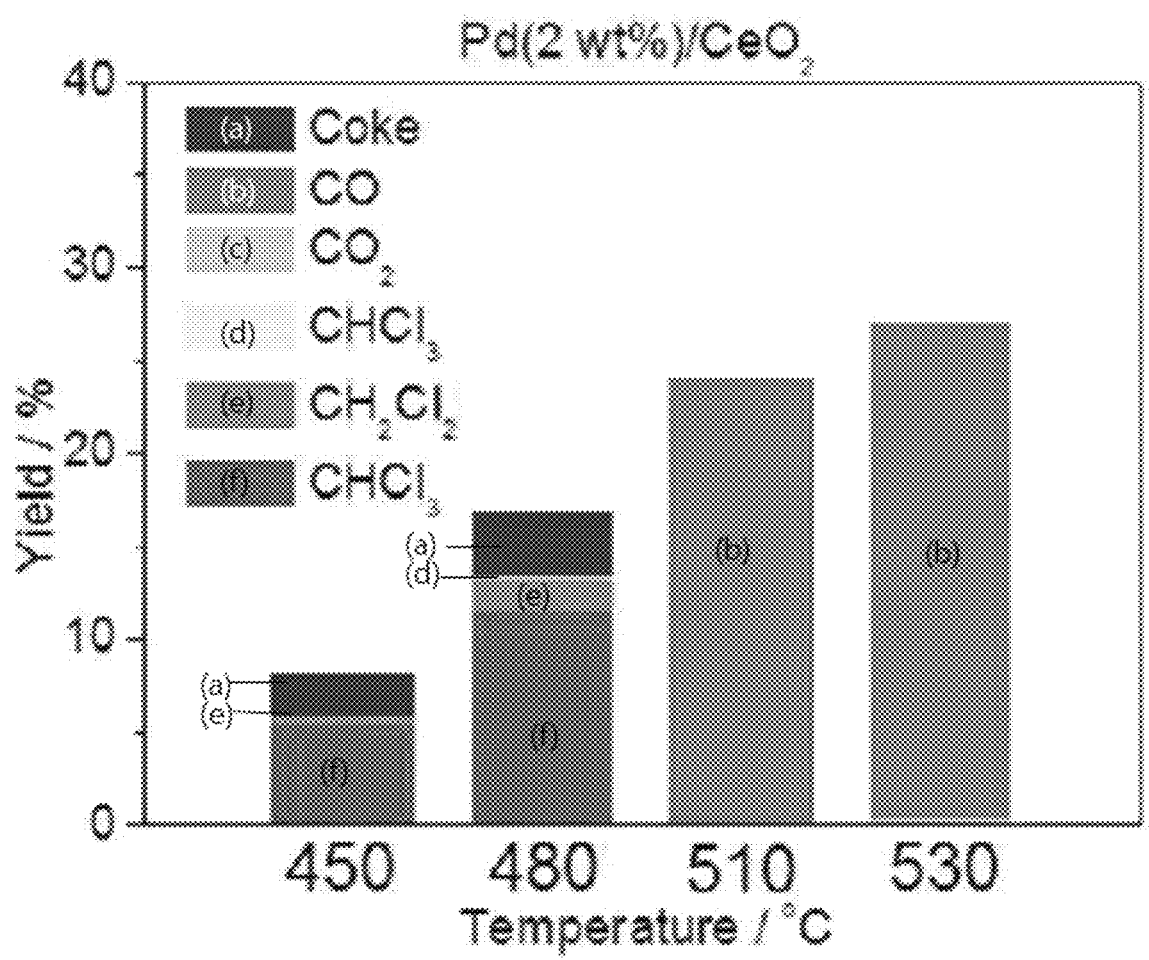

[Figure 5]
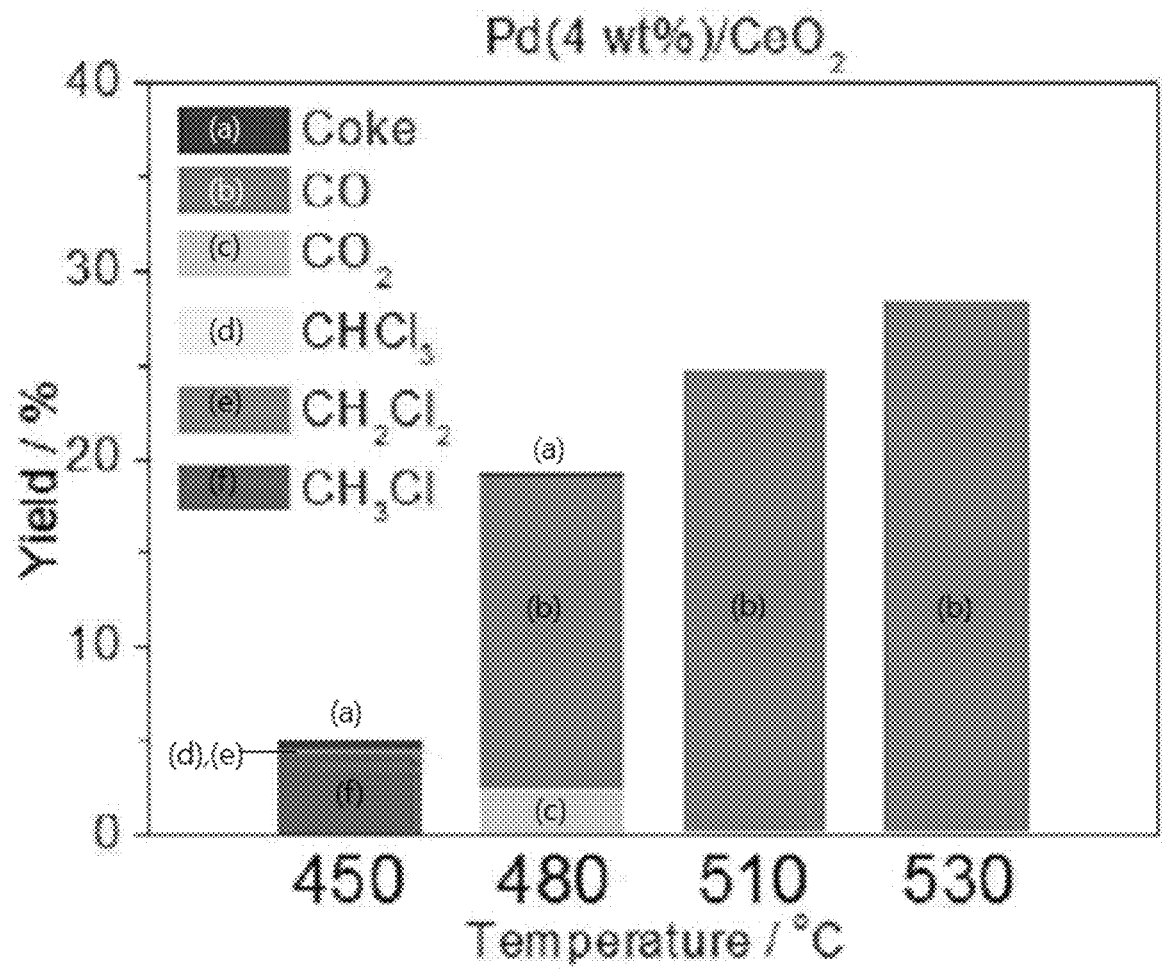

[Figure 6]
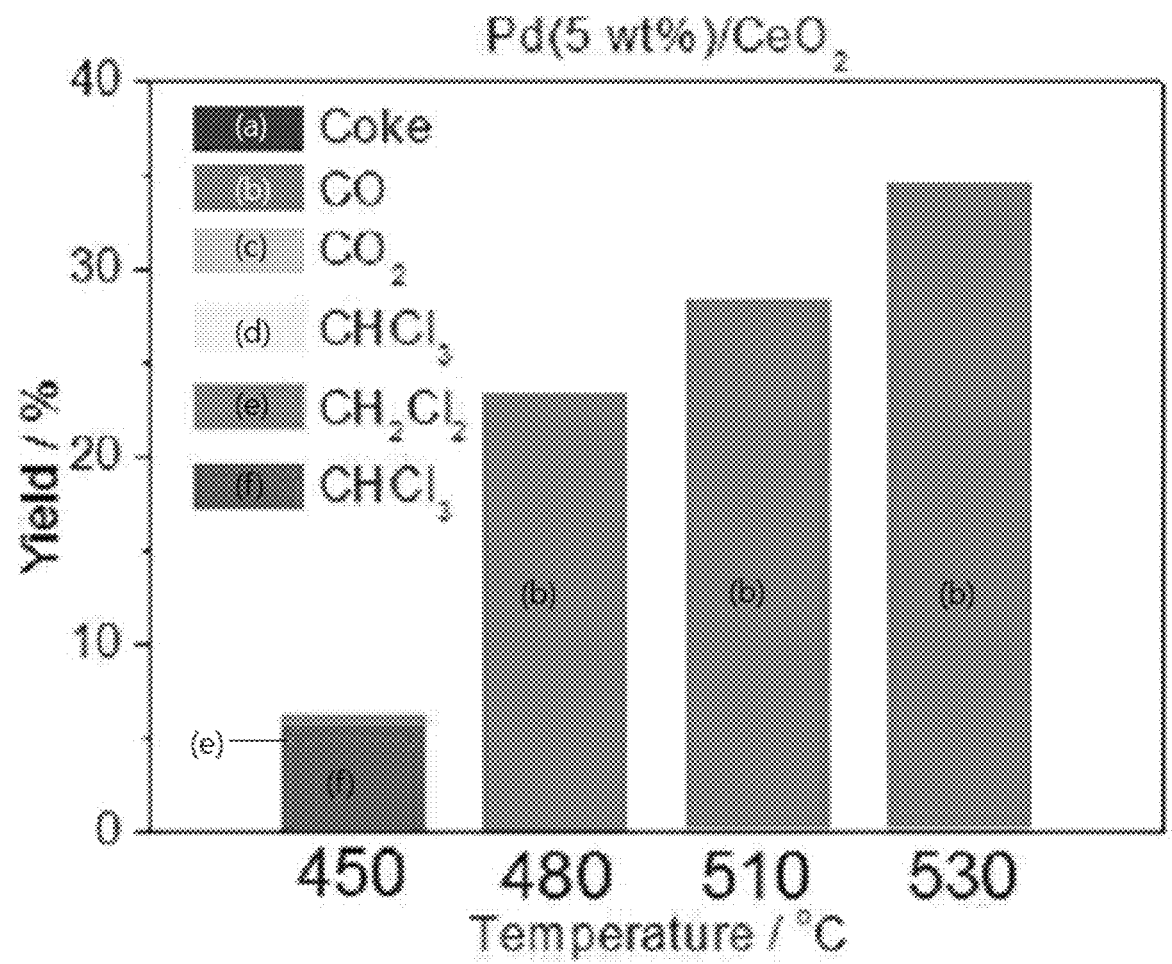

[Figure 7]
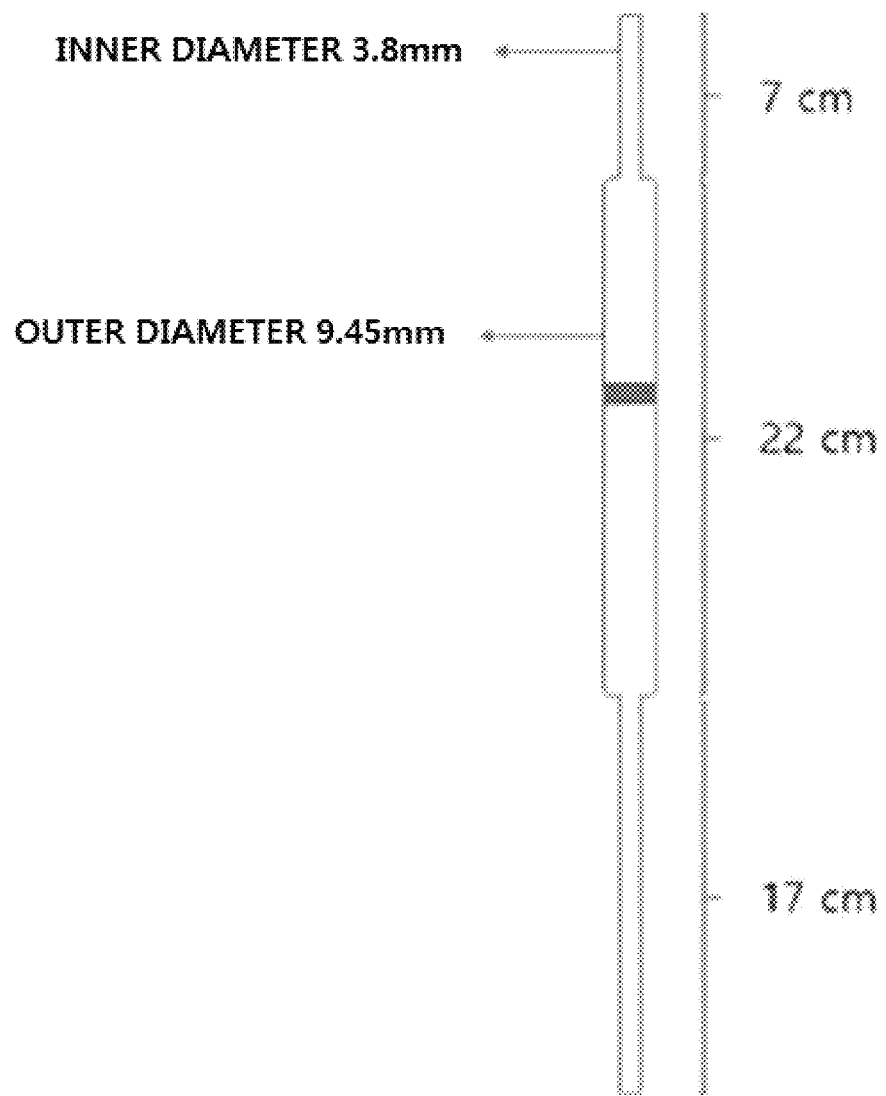

PARTIAL OXIDATION PROCESS OF HYDROCARBONS

TECHNICAL FIELD

This application claims priority to and the benefit of Korean Patent Application No. 10-2018-0029319 filed in the Korean Intellectual Property Office on Mar. 13, 2018, the entire contents of which are incorporated herein by reference.

The present specification relates to a partial oxidation process of hydrocarbons.

BACKGROUND ART

The importance of studies on the method of utilizing natural gas which is cheap and rich in reserves due to the continuous increase in oil prices has been further increased, and the prior arts concerning pyrolysis reactions of methane in natural gas using oxygen and coupling reactions of methane in natural gas using a catalyst have been mainly reported. Further, as a method in the related art that may use a chlorine compound for the activation of methane, methods of pyrolyzing methane and chlorine at high temperature are disclosed in U.S. Pat. Nos. 4,199,533, 4,804,797, 4,714,796 and 4,983,783, and the like. However, since a high-temperature pyrolysis method of methane by chlorine depends on the amount of heat supplied and the reaction time, which are simply provided, in the control of selectivity, lots of byproducts such as methylene chloride or coke are additionally generated.

PRIOR ART DOCUMENT

[Patent Document]
Korean Patent Application Laid-Open No. 10-2010-0074017

DETAILED DESCRIPTION OF INVENTION

Technical Problem

The present specification provides a partial oxidation process of hydrocarbons.

Technical Solution

The present specification provides a partial oxidation process of hydrocarbons, which is performed by bringing an inlet gas comprising a hydrocarbon raw material gas and a hydrogen chloride gas into contact with a catalyst, in which the catalyst is a catalyst in which a catalyst material comprising palladium (Pd) is supported on a carrier comprising cerium oxide ($CeO_2$) and an amount of catalyst material supported is 2 wt % to 10 wt % based on a total weight of the catalyst.

Advantageous Effects

By a partial oxidation process of hydrocarbons according to an exemplary embodiment of the present specification, a high conversion may be achieved even at low temperature.

By the partial oxidation process of hydrocarbons according to an exemplary embodiment of the present specification, the production of coke may be minimized.

By the partial oxidation process of hydrocarbons according to an exemplary embodiment of the present specification, an amount of complete oxide such as carbon dioxide produced may be decreased and an amount of synthetic gas such as carbon monoxide produced may be increased.

By the partial oxidation process of hydrocarbons according to an exemplary embodiment of the present specification, a catalyst of which the activity is maintained even during operation for a long period of time is used, thereby obtaining carbon monoxide with a high yield.

BRIEF DESCRIPTION OF DRAWINGS

FIG. 1 illustrates a XRD analysis of a catalyst according to Preparation Example 3 according to each condition.

FIG. 2 illustrates a yield of each product according to Experimental Example 1.

FIG. 3 illustrates the results of a test of using a catalyst according to Experimental Example 2 for a long period of time.

FIG. 4 illustrates the selectivity of each product when a catalyst of Preparation Example 1 is allowed to react according to the temperature in Experimental Example 4.

FIG. 5 illustrates the yield of each product when a catalyst of Preparation Example 2 is allowed to react according to the temperature in Experimental Example 4.

FIG. 6 illustrates the yield of each product when a catalyst of Preparation Example 3 is allowed to react according to the temperature in Experimental Example 4.

FIG. 7 illustrates a reactor used in each Experimental Example.

BEST MODE

Hereinafter, the present specification will be described.

When one member is disposed "on" another member in the present specification, this comprises not only a case where the one member is brought into contact with another member, but also a case where still another member is present between the two members.

When one part "comprises" one constituent element in the present specification, unless otherwise specifically described, this does not mean that another constituent element is excluded, but means that another constituent element may be further included.

In an exemplary embodiment of the present specification, the hydrocarbon raw material gas is a gas comprising carbon and hydrogen, and means a gas which is a raw material for a target product. Examples thereof comprise: straight-chained or branched saturated aliphatic hydrocarbons having 1 to 16 carbon atoms, such as methane, ethane, propane, butane, pentane, hexane, heptane, octane, nonane, and decane; alicyclic saturated hydrocarbons, such as cyclohexane, methylcyclohexane, and cyclooctane; monocyclic and polycyclic aromatic hydrocarbons; and hydrocarbons such as urban gas, LPG, naphtha and a kerosene.

In an exemplary embodiment of the present specification, an inlet gas means a collection of gases flowing into a reactor, and is differentiated from an outlet gas discharged outside the reactor after the reaction.

In an exemplary embodiment of the present specification, the partial oxidation process of hydrocarbons may be expressed as 'process', and may be called a partial oxidation method of hydrocarbons or a partial oxidation modification method of hydrocarbons, in the present specification.

In an exemplary embodiment of the present specification, the partial oxidation process of hydrocarbons is intended to decrease an amount of complete oxide such as carbon dioxide produced and increase an amount of synthetic gas such as carbon monoxide produced.

In an exemplary embodiment of the present specification, the inlet gas comprises a hydrogen chloride gas. The hydrogen chloride gas (HCl) means hydrogen chloride in a gas state, and is introduced in order to maintain the activity of a catalyst.

The present specification provides a partial oxidation process of hydrocarbons, which is performed by bringing an inlet gas comprising a hydrocarbon raw material gas and a hydrogen chloride gas into contact with a catalyst, in which the catalyst is a catalyst in which a catalyst material comprising palladium (Pd) is supported on a carrier comprising cerium oxide ($CeO_2$) and an amount of catalyst material supported is 2 wt % to 10 wt % based on a total weight of the catalyst. The catalyst is a catalyst in which a catalyst material comprising palladium (Pd) is supported on a carrier comprising cerium oxide ($CeO_2$), and as an inlet gas to be injected into a reactor comprises a hydrogen chloride gas, the excellent activity of the catalyst may be maintained. Specifically, since the form of the catalyst is changed into a form in which the activity is excellent by the hydrogen chloride gas component, the excellent catalyst activity is maintained.

Actually, in the reactor, a catalyst (Pd/$CeO_2$) in which palladium (Pd) is supported on a cerium oxide ($CeO_2$) carrier is changed into a form of (Pd/CdOCl) due to a hydrogen chloride gas included in the inlet gas, and the Pd/CeOCl catalyst exhibits excellent activity as compared to a catalyst having a Pd/$CeO_2$ structure. In order to maintain the structural form of Pd/CeOCl, the hydrogen chloride gas (HCl) needs to be continuously injected. However, when the injection of the hydrogen chloride gas is stopped or the hydrogen chloride gas is not included in the inlet gas, the catalyst is present in the form of Pd/$CeO_2$, so that the activity of the catalyst deteriorates. The presence or absence of CeOCl may be confirmed through X-ray diffraction (XRD) data of the catalyst, and is as shown in FIG. 1.

However, the partial oxidation process of hydrocarbons according to an exemplary embodiment of the present specification may maintain the excellent activity of the catalyst by comprising the hydrogen chloride gas in the inlet gas.

In an exemplary embodiment of the present specification, the partial oxidation reaction of hydrocarbons is performed by bringing an inlet gas comprising a hydrocarbon raw material gas and a hydrogen chloride gas into contact with a catalyst. The meaning of the contact may be explained by a catalyst theory. Specifically, a catalyst comprises a certain active site or active center, and a catalytic action is performed at the active site or active center. While the inlet gas is brought into contact with the active site or active center, the catalytic reaction occurs. For example, there is a method of loading a catalyst into a reactor and circulating the inlet gas in the reactor.

In an exemplary embodiment of the present specification, the ratio of the volume flow rates of the hydrocarbon raw material gas to the hydrogen chloride gas may be 1:1 to 10:1, preferably 1:1 to 5:1, more preferably 1:1 to 3:1, and most preferably 1.5:1 to 2.5:1. When the ratio satisfies the numerical range, the above-described structural form of Pd/CeOCl by hydrogen chloride may be maintained while the reaction proceeds, so that the excellent activity of the catalyst may be maintained. Accordingly, there is an advantage in that the selectivity of the target product may be maintained at a high level.

In an exemplary embodiment of the present specification, the inlet gas further comprises an oxygen gas, and the ratio of the volume flow rates of the hydrocarbon raw material gas to the oxygen gas may be 1:1 to 10:1, preferably 1:1 to 6:1, and more preferably 3:1 to 5:1. When the oxygen gas flow rate exceeds the range, there is a problem in that the production of a byproduct $CO_2$ is increased. The ratio of the volume flow rates may be measured by a method generally used in the art to which the technology pertains, and may be achieved by adjusting the temperature and pressure of an inlet gas flowing into a reactor. For example, the ratio of the volume flow rates may be measured at an inlet gas temperature of 25° C. and a pressure of 1 atm, and may be measured by using a volumetric flow meter generally used in the art.

In an exemplary embodiment of the present specification, the partial oxidation process of hydrocarbons may be performed at a process temperature of 450° C. to 600° C. and a pressure of 0.5 atm to 3 atm. When the process temperature and the pressure satisfy the ranges, it is possible to suppress byproducts from being produced, and particularly, to suppress coke from being generated.

In an exemplary embodiment of the present specification, the process temperature may be 450° C. to 580° C., 470° C. to 550° C., or 500° C. to 550° C. When the process temperature satisfies the range, it is possible to suppress byproducts from being produced and to increase the selectivity of a target product.

In an exemplary embodiment of the present specification, the process may be performed under a pressure of 0.5 atm to 3 atm, 0.5 atm to 2 atm, preferably, 0.5 atm to 1.5 atm.

In an exemplary embodiment of the present specification, the space velocity of the inlet gas may be 10,000 ml/(h·gcat) to 50,000 ml/(h·gcat). When the space velocity of the inlet gas satisfies the range, the inlet gas is sufficiently fluid, so that it is possible to effectively suppress coke from being generated.

In an exemplary embodiment of the present specification, the inlet gas further comprises one or two or more inert gases selected from the group consisting of nitrogen, helium, argon, and carbon dioxide.

In an exemplary embodiment of the present specification, the ratio of the volume flow rates of the hydrocarbon raw material gas to the inert gas may be 1:1 to 1:5.

In an exemplary embodiment of the present specification, a partial oxidation process of hydrocarbons may be performed in a reactor generally used in the art to which the technology pertains. Examples of the reactor comprise a packed bed reactor, a fluidized bed reactor, or a circulating fluidized bed reactor.

In an exemplary embodiment of the present specification, the amount of catalyst material supported may be 2 wt % to 10 wt %, 2 wt % to 8 wt %, preferably 3 wt % to 6 wt %, more preferably 4 wt % to 5.5 wt %, and most preferably 5 wt %, based on a total weight of the catalyst. When the amount of catalyst material supported satisfies the numerical range, there is an advantage in that the activity of the catalyst is excellent and the production of byproducts may be suppressed. Specifically, when the amount of catalyst material supported is within the weight range, the amount of CeOCl produced is increased, so that there is an effect in that the number of the active sites of the catalyst is increased.

The amount of catalyst material supported may be measured by a method generally used in the art to which the technology pertains. For example, it is possible to confirm the presence or absence and wt % of an atom corresponding to the catalyst material by the energy dispersive spectroscopy (EDS) measurement. The EDS analysis is used to confirm the chemical composition of a sample along with SEM photographs.

An exemplary embodiment of the present specification provides a partial oxidation process of hydrocarbons, which is performed by bringing an inlet gas comprising a hydrocarbon raw material gas and a hydrogen chloride gas into contact with a catalyst, in which the catalyst is a catalyst in which palladium (Pd) is supported on a carrier comprising cerium oxide ($CeO_2$) and an amount of palladium (Pd) supported is 2 wt % to 10 wt % based on a total weight of the catalyst.

In an exemplary embodiment of the present specification, a content of the palladium may be 50 wt % to 100 wt %, preferably 90 wt % to 100 wt %, and more preferably 100%, based on 100 parts by weight of the catalyst material. The content of the palladium of 100 wt % means that only palladium is supported on the carrier.

In an exemplary embodiment of the present specification, the amount of palladium (Pd) supported may be 2 wt % to 10 wt %, 2 wt % to 8 wt %, preferably 3 wt % to 6 wt %, more preferably 4 wt % to 5.5 wt %, and most preferably 5 wt %, based on a total weight of the catalyst. When the amount of palladium supported satisfies the numerical range, there is an advantage in that the activity of the catalyst is excellent and the production of byproducts may be suppressed. Specifically, when the amount of palladium supported is within the weight range, the amount of CeOCl produced is increased, so that there is an effect in that the number of the active sites of the catalyst is increased.

The amount of palladium (Pd) supported may be measured by a method generally used in the art to which the technology pertains. For example, it is possible to confirm the presence or absence and wt % of a Pd atom by the energy dispersive spectroscopy (EDS) measurement. The EDS analysis is used to confirm the chemical composition of a sample along with SEM photographs.

In an exemplary embodiment of the present specification, the amount of catalyst material or palladium (Pd) supported may be adjusted in order to maximize the selectivity of a target product according to the process temperature.

In an exemplary embodiment of the present specification, the amount of palladium (Pd) supported may be 2 wt % to 4 wt % based on the total weight of the catalyst and the process temperature may be 490° C. to 600° C., and preferably, the amount of palladium (Pd) supported may be 2.5 wt % to 3 wt % based on the total weight of the catalyst and the process temperature may be 500° C. to 550° C.

In an exemplary embodiment of the present specification, the amount of palladium (Pd) supported may be 3 wt % to 6 wt % based on the total weight of the catalyst and the process temperature may be 460° C. to 600° C., and preferably, the amount of palladium (Pd) supported may be 4.5 wt % to 5.5 wt % based on the total weight of the catalyst and the process temperature may be 470° C. to 550° C.

In an exemplary embodiment of the present specification, one or two or more catalyst materials selected from the group consisting of scandium (Sc), yttrium (Y), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), platinum (Pt), rhodium (Rh), osmium (Os), iridium (Ir), and zirconium (Zr) may be further supported on the carrier.

In an exemplary embodiment of the present specification, the carrier may comprise cerium oxide in an amount of 50 wt % to 100 wt % based on the total weight of the carrier.

When the content of cerium oxide satisfies the numerical range, the performance of the catalyst itself may be improved by cerium oxide because the content of cerium oxide included in the carrier is large.

In an exemplary embodiment of the present specification, the carrier may have a cerium oxide ($CeO_2$) single composition. The cerium oxide ($CeO_2$) single composition means that the carrier rarely comprises materials other than cerium oxide, or comprises a small amount of materials other than cerium oxide even though the carrier comprises the materials. For example, the content of cerium oxide may be 80 wt % or more, 90 wt % or more, 95 wt % or more, or 99 wt % or more, and most preferably 100 wt %, based on the total 100 weight of the carrier.

It is possible to confirm, by a general method used in the art to which the technology pertains, that the carrier has a cerium oxide ($CeO_2$) single composition. For example, it is possible to confirm the presence or absence of $CeO_2$ by confirming X-ray diffraction peak patterns. Specifically, when peaks corresponding to (111), (200), (220), and (311) crystal planes are present, it is possible to confirm that cubic phase $CeO_2$ is present. Further, it is possible to confirm the presence or absence and wt % of Ce and O atoms by the energy dispersive spectroscopy (EDS) measurement. The EDS analysis is used to confirm the chemical composition of a sample along with SEM photographs. During the EDS measurement on cerium oxide, peaks corresponding to Ce and O atoms are observed. In contrast, when a peak of an atom other than Ce and O atoms is rarely observed, it is possible to confirm that the carrier has a cerium oxide single composition.

In an exemplary embodiment of the present specification, the carrier may be composed of only cerium oxide.

In an exemplary embodiment of the present specification, the carrier comprising cerium oxide ($CeO_2$) may be in the form of a powder, the powder may be in the form of a sphere, and the diameter of a catalyst comprising the carrier will be described below.

In an exemplary embodiment of the present specification, the carrier may further comprise a composite oxide comprising one or more elements selected from the group consisting of Zr, Y, an alkali metal element, an alkaline earth metal element, a lanthanide element, and a rare earth element. Specific examples on the alkali metal element, the alkaline earth metal element, the lanthanide element, and the rare earth element are the same as those described above.

In an exemplary embodiment of the present specification, the alkali metal element means the other chemical elements except hydrogen in Group 1 of the Periodic Table, and may be lithium (Li), sodium (Na), potassium (K), rubidium (Rb), cesium (Cs), or francium (Fr).

In an exemplary embodiment of the present specification, the alkaline earth metal element means an element of Group 2 of the Periodic Table, and may be beryllium (Be), magnesium (Mg), calcium (Ca), strontium (Sr), barium (Ba), or radium (Ra).

In an exemplary embodiment of the present specification, the rare earth element may be scandium (Sc), yttrium (Y), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), or lutetium (Lu).

In an exemplary embodiment of the present specification, examples of the composite oxide comprise a CeZr composite oxide (70:30), a CeZrLa composite oxide (86:10:4), a CeZrLa composite oxide (66:29:5), a CeZrLaY composite oxide (40:50:5:5), a CeZrPr composite oxide (40:55:5), a CeZrLaNdPr composite oxide, a CeZrNdPrCa composite oxide, or the like. The numbers in the parenthesis in the latter part mean the ratios of the weights of respective elements.

In an exemplary embodiment of the present specification, the carrier may have a specific surface area of 50 $m^2/g$ to 250 $m^2/g$, 100 $m^2/g$ to 200 $m^2/g$, preferably 120 $m^2/g$ to 150 $m^2/g$. When the specific surface area of the carrier satisfies the numerical range, the wide contact area with an active component of the catalyst may be secured, and when an inlet gas is delivered into the catalyst, the material delivery resistance is appropriately controlled, so that the excellent conversion of the raw material gas may be achieved. The specific surface area of the carrier may mean the area ($m^2$) based on the total weight (g) of the carrier. The specific surface area of the carrier may be measured by a method generally used in the art, and may be measured, for example, by the Brunauer, Emmett and Teller (BET) method. The method is a type of a vapor adsorption method that adsorbs molecules or ions onto the surface of a carrier and measures the surface area from the amount of molecules or ions adsorbed, and after a sample is stored at 250° C. for 5 hours, the specific surface area may be measured by using an $N_2$ adsorption-desorption isotherm using the Micromeritics ASAP 2010 apparatus.

In an exemplary embodiment of the present specification, the catalyst may have a diameter of 0.1 mm to 10 mm, 0.1 mm to 1.0 mm, preferably 0.1 mm to 0.5 mm, and more preferably 0.18 mm to 0.25 mm. When the catalyst diameter is less than 0.1 mm, a pressure drop phenomenon in a reactor significantly occurs, so that the conversion or reaction rate of a reactant may deteriorate. In contrast, when the catalyst diameter is more than 1.0 mm, a channeling phenomenon in which a reactant does not go through a catalyst layer may occur. The diameter of the catalyst may mean an average particle diameter of catalyst particles. The diameter of the catalyst may be measured by a method generally used in the art, and for example, the respective diameters of two or more catalyst particles may be measured by using a scanning electron microscope (SEM), and then an average of the measured diameters of the particles may be calculated as an average particle diameter.

An exemplary embodiment of the present specification provides a method for preparing the above-described catalyst for a partial oxidation process of hydrocarbons.

An exemplary embodiment of the present specification provides a method for preparing a catalyst for a partial oxidation process of hydrocarbons, the method comprising: preparing a carrier comprising cerium oxide ($CeO_2$); and supporting a catalyst material comprising palladium (Pd) on the carrier.

In an exemplary embodiment of the present specification, the supporting of the catalyst material comprising palladium (Pd) on the carrier may be performed by a method of putting the carrier into an aqueous precursor solution comprising an active material precursor comprising palladium (Pd) and stirring the resulting solution.

In an exemplary embodiment of the present specification, the supporting of the catalyst material comprising palladium (Pd) on the carrier may further comprise: supporting palladium (Pd) on the carrier; and supporting one or two or more catalyst materials selected from the group consisting of scandium (Sc), yttrium (Y), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), platinum (Pt), rhodium (Rh), osmium (Os), iridium (Ir), and zirconium (Zr). The supporting of the catalyst material comprising palladium (Pd) on the carrier may be performed by a method of putting the carrier into an aqueous precursor solution comprising an active material precursor and stirring the resulting solution.

In an exemplary embodiment of the present specification, the active material precursor may vary depending on the type of target material. For example, when the active material is copper, the active material precursor may be copper chloride dihydrate ($CuCl_2.2H_2O$), and when the active material is iron (Fe), the active material precursor may be $Fe(NO_3)_3.9H_2O$, and when the active material is potassium, the active material precursor may be potassium chloride (KCl), and when the active material is lanthanum, the active material precursor may be lanthanum chloride heptahydrate ($LaCl_3.7H_2O$), and when the active material is palladium, the palladium precursor may be palladium (II) nitrate dihydrate ($Pd(NO_3)_2.2H_2O$).

In an exemplary embodiment of the present specification, the stirring may be performed such that the aqueous precursor solution is supported on the carrier well, and may be performed for 0.5 hour or more, preferably, 1 hour or more.

In an exemplary embodiment of the present specification, the method for preparing a catalyst for a partial oxidation process of hydrocarbons may comprise: drying a catalyst; and calcining the catalyst.

In an exemplary embodiment of the present specification, the drying of the catalyst is for evaporating moisture of the catalyst, and the method of drying the catalyst is not particularly limited as long as the method is generally used in the art to which the technology pertains. For example, the drying of the catalyst may be performed by a method of evaporating moisture using a rotary evaporator and drying the catalyst at a temperature of 100° C. for 10 hours or more.

In an exemplary embodiment of the present specification, the calcining of the catalyst is performed to remove a precursor material remaining in the catalyst after the supporting of the catalyst material, and a method of calcining the catalyst is not particularly limited as long as the method is generally used in the art to which the technology pertains, and may be performed at a temperature of 100° C. or more for 1 to 10 hours, for example. When the method of calcining the catalyst satisfies the performance temperature and the performance time, it is possible to effectively remove the precursor material, and to suppress a problem with deterioration in durability caused by the occurrence of phase change in carrier.

MODE FOR INVENTION

Hereinafter, the above-described contents will be described through Examples. However, the right scope of the present specification is not limited by the following Examples.

Preparation Example 1

A cerium oxide carrier ($CeO_2$) powder (3 g, from Rhodia®, surface area of 130 $m^2/g$ or more: 135 $m^2/g$) was prepared as a carrier. Palladium (Pd) as a catalyst material was supported on the $CeO_2$ carrier by following method. In this case, palladium (II) nitrate dihydrate($Pd(NO_3)_2.2H_2O$) was used as a palladium (Pd) precursor.

A precursor solution was prepared by weighing the calculated amount of precursor and dissolving the precursor in distilled water, the cerium oxide carrier was produced in a powder state and then put into the precursor solution and stirred sufficiently for 1 hour, and then the palladium was supported on the cerium oxide carrier by evaporating water using a rotary evaporator. Thereafter, a catalyst was prepared by drying the carrier at a temperature of 100° C. for about 12 hours or more, and then firing the dried carrier at a temperature of 600° C. for 6 hours.

Finally, the catalyst with palladium (Pd) supported on the $CeO_2$ carrier was prepared, the amount of palladium (Pd) supported was 2 wt % based on the total weight of the catalyst {sum of the weights of the $CeO_2$ carrier and palladium (Pd)}, and the diameter of the catalyst was adjusted to 0.18 mm to 0.25 mm by using a sieve.

Preparation Example 2

A catalyst was prepared in the same manner as in Preparation Example 1, except that the amount of palladium supported was 4 wt % based on the total weight of the catalyst.

Preparation Example 3

A catalyst was prepared in the same manner as in Preparation Example 1, except that the amount of palladium supported was 5 wt % based on the total weight of the catalyst.

With respect to the catalyst according to Preparation Example 3, the X-ray diffraction (XRD) diagrams before and after the respective reactions are shown in FIG. 1.

Line (a) in FIG. 1 illustrates a $CeO_2$ carrier before palladium is supported.

Line (b) in FIG. 1 illustrates $Pd/CeO_2$ before the catalyst with palladium supported in Preparation Example 3 is allowed to react.

Line (c) in FIG. 1 illustrates $Pd/CeO_2$ after the catalyst in Preparation Example 3 is allowed to react at 450° C.

Line (d) in FIG. 1 illustrates Pd/CeOCl after the catalyst in Preparation Example 3 is allowed to react at 480° C.

Line (e) in FIG. 1 illustrates Pd/CeOCl when the catalyst in Preparation Example 3 is allowed to react at 510° C.

In FIG. 1, a peak marked with *CeOCl indicates the presence of CeOCl. From the result in FIG. 1, it could be confirmed that in the case of the catalyst in Preparation Example 3, when the catalyst was allowed to react at a temperature of 480° C. or more, the catalyst was changed into the form of CeOCl.

Preparation Example 4

A catalyst was prepared in the same manner as in Preparation Example 1, except that the amount of palladium supported was 7.5 wt % based on the total weight of the catalyst.

Preparation Example 5

A catalyst was prepared in the same manner as in Preparation Example 1, except that the amount of palladium supported was 10 wt % based on the total weight of the catalyst.

Preparation Example 6

A catalyst was prepared in the same manner as in Preparation Example 1, except that the amount of palladium supported was 0.5 wt % based on the total weight of the catalyst.

Experimental Example 1: Examples 1 to 5 and Comparative Example 1

In order to compare the effects according to the amount of palladium supported, each experiment was performed under the test conditions described below.

Test Conditions

A packed bed reactor (PBR) formed of a quartz material as illustrated in FIG. 7 was applied to the experiment. The portion indicated with a blue color in the drawing was loaded with the catalysts according to the Preparation Examples. The process temperature was adjusted by using a thermocouple provided outside the packed bed reactor.

The composition of the inlet gas was composed of a volume ratio of $CH_4:O_2:HCl:Ar:N_2=4:1:2:3:10$, and the volume flow rate ($u_0$) of the inlet gas and the ratio $[F_T/W_{cat}]$ of flow rate/catalyst weight were adjusted to 50 ml/min and 30,000 ml/(h·$g_{cat}$), respectively, by adjusting the pressure in the reactor. The $CH_4$, $O_2$, and HCl are reactant gases, and the Ar acts as a diluent. In this case, the pressure in the reactor was normal pressure (1 atm).

After all the gas conditions were completely set, an experiment was started after the reactor was pre-heated up to 450° C., and the selectivity of the catalyst used in each case was monitored. While the reaction was performed, the temperature in the reactor was maintained at 510° C.

The concentration of gas produced was measured by a gas chromatograph (GC) downstream. The concentrations of $CH_4$, $CH_3Cl$, $CH_2Cl_2$, and $CHCl_3$ were measured by a flame ionization detector (FID), and the concentrations of $CH_4$, $N_2$, $O_2$, $CO_2$, and CO were measured by a thermal conductivity detector (TCD).

The yield and selectivity associated with the gas may be calculated by the following Mathematical Formulae 1 to 3. The correction factor (α) associated with the inlet and outlet nitrogen gas is calculated by the following Mathematical Formula 1.

$$\alpha = \frac{n(N_2)_{inlet}}{n(N_2)_{outlet}} \quad \text{[Mathematical Formula 1]}$$

The $n(N_2)_{inlet}$ is the number of moles of a nitrogen gas flowing into the reactor, and the $n(N_2)_{outlet}$ is the number of moles of a nitrogen gas flowing out of the reactor.

The methane conversion (X, %) is calculated by the following Mathematical Formula 2.

$$X(CH_4) = \frac{n(CH_4)_{inlet} - \alpha \times n(CH_4)_{outlet}}{n(CH_4)_{inlet}} \times 100(\%) \quad \text{[Mathematical Formula 2]}$$

The $n(CH_4)_{inlet}$ is the number of moles of a methane gas flowing into the reactor, and the $n(CH_4)_{outlet}$ is the number of moles of a methane gas flowing out of the reactor.

The selectivity (S) of the gas produced is calculated by the following Mathematical Formula 3.

$$S(j) = \frac{n(j)_{outlet}}{\Sigma n(j)_{outlet}} \times 100(\%) \quad \text{[Mathematical Formula 3]}$$

The $n(j)_{outlet}$ is the number of moles of each produced gas flowing out of the reactor, and the $\Sigma n(j)_{outlet}$ is the total number of moles of the produced gases.

In this case, the process temperature was 510° C., and the conversion of the reactant and the selectivity of the product are shown in the following Table 1.

TABLE 1

| Classification | Configuration/Type | | Example 1 | Example 2 | Example 3 | Example 4 | Example 5 | Comparative Example 1 |
|---|---|---|---|---|---|---|---|---|
| Catalyst composition | Type of catalyst | | Preparation Example 1 | Preparation Example 2 | Preparation Example 3 | Preparation Example 4 | Preparation Example 5 | Preparation Example 6 |
| | Amount (wt %) of palladium supported | | 2 wt % | 4 wt % | 5 wt % | 7.5 wt % | 10 wt % | 0.5 wt % |
| Experimental Example 1 | Process temperature (° C.) | | 510° C. | 510° C. | 510° C. | 510° C. | 510° C. | 510° C. |
| | Conversion (%) of methane | | 22.4 | 23.5 | 28.3 | 28.5 | 27.9 | 22 |
| | Selectivity (%) of product | $CH_3Cl$ | 0 | 0 | 0 | 0 | 0 | 56 |
| | | $CH_2Cl_2$ | 0 | 0 | 0 | 0 | 0 | 14 |
| | | $CHCl_3$ | 0 | 0 | 0 | 0 | 0 | 0.3 |
| | | $CO_2$ | 0 | 1.2 | 0.7 | 1.1 | 1.2 | 6 |
| | | CO | 100 | 98.8 | 99.3 | 98.3 | 98.8 | 0 |
| | | Coke | 0 | 0 | 0 | 0.6 | 0 | 23.6 |

In the case of Comparative Example 1, it could be confirmed that palladium was supported in an amount of less than 2 wt % on the catalyst, and as a result, byproducts ($CH_3Cl$, $CH_2Cl_2$, $CHCl_3$, and Coke) were generated. This is because the amount of palladium was small, so that CeOCl was not sufficiently produced from $CeO_2$, and accordingly, a side reaction occurred in $CeO_2$. In particular, in the case of Comparative Example 1, it could be confirmed that coke was generated, and the coke is deposited on the surface of the catalyst to decrease the number of active sites, so that a phenomenon in which the catalyst is inactivated may occur. In the case of Examples 1 to 5, it could be confirmed that palladium was supported in an amount of 2 wt % or more on the used catalyst, so that coke was rarely generated and other byproducts were not produced because the reaction gases sufficiently reacted.

In particular, in the case of Examples 1 to 3, the selectivity of CO as the target product was 98% or more, which exhibited an excellent result. This is a result which was obtained as, when the amount of palladium supported was 2 to 5 wt %, the reaction gases sufficiently reacted and the number of active sites in the catalyst was also appropriately maintained. Most preferably, the case where the amount of palladium supported was 4 wt % or 5 wt % exhibited a result that the selectivity of CO was close to 100%, the selectivity of other byproducts was close to 0%, and the conversion of methane was high.

Meanwhile, in relation to the experimental results, the selectivity of each product according to the amount of palladium supported is shown in FIG. 2. In FIG. 2, the x axis indicates the amount of palladium supported in the catalyst prepared in each Preparation Example, and the y axis indicates the selectivity of the produced gas.

Experimental Example 2

The performance of the catalyst according to the long-term use was compared by using the catalyst according to Preparation Example 3. The comparison is illustrated in FIG. 3, and it could be confirmed that even though a long time elapsed after the reaction proceeded, the activity of the catalyst was maintained. $X(CH_4)$ indicates the conversion of a methane gas, and S(X) indicates the selectivity of a gas component x. Further, the x axis and the y axis indicate the reaction progress time and the conversion or selectivity of each gas, respectively.

Experimental Example 3

An experiment was performed under the test conditions described below for a comparison with a case where no hydrogen chloride gas was present in an inlet gas.

An experiment was performed in the same manner as in Experimental Example 1, except that the composition of the inlet gas was changed into a volume ratio of $CH_4:O_2:N_2$=4:1:15, and the temperature was changed into the temperature in Table 2. That is, the hydrogen chloride gas was not included in the inlet gas. As the catalyst, the catalyst in Preparation Example 3 was used. That is, the amount of palladium supported in the catalyst was 5 wt %.

In relation to the experiment, the selectivity of each product according to whether the hydrogen chloride gas was included in the inlet gas is shown in the following Table 2.

TABLE 2

| Reaction temperature | Whether hydrogen chloride gas is included in inlet gas | Product selectivity (%) | |
|---|---|---|---|
| | | $CO_2$ | CO |
| 480° C. | X | 71 | 29 |
| 510° C. | X | 56 | 44 |
| 480° C. | ○ | 0.8 | 99.2 |
| 510° C. | ○ | 0.7 | 99.3 |

From the experimental results, it could be confirmed that when no hydrogen chloride gas was included in the inlet gas, the selectivity of the product was notably decreased even though the same catalyst was used. The result is because when no hydrogen chloride gas is included in the inlet gas, the catalyst is in the form of $Pd/CeO_2$, and the activity thereof is notably decreased. In contrast, the result is because when the hydrogen chloride gas is included in the inlet gas, the catalyst is changed into the form of Pd/CeOCl by the hydrogen chloride gas, so that the activity caused by the catalyst structure is increased. In this case, it could be confirmed that the selectivity of CO was 99% or more.

Experimental Example 4

In order to confirm that when the process temperature was adjusted, the selectivity of the target product could be changed according to the amount of palladium supported, the following experiment was performed. The selectivity of each product was calculated while the process temperature was adjusted by using the catalysts according to Preparation Examples 1 to 3, and the results are as follows. Other process conditions are the same as those in Experimental Example 1.

TABLE 3

| Type of catalyst | | Preparation Example 1 | | | | Preparation Example 2 | | | | Preparation Example 3 | | | |
|---|---|---|---|---|---|---|---|---|---|---|---|---|---|
| Catalyst Composition Experimental Example 3 | Amount (wt %) of palladium supported | 2 wt % | | | | 4 wt % | | | | 5 wt % | | | |
| | Conversion (%) of methane | 8.1 | 16.8 | 22.4 | 27.6 | 5.1 | 19.1 | 23.5 | 26.8 | 6.3 | 23.4 | 28.3 | 34.6 |
| | Process temperature (° C.) | 450 | 480 | 510 | 530 | 450 | 480 | 510 | 530 | 450 | 480 | 510 | 530 |
| | Product selectivity (%) $CH_3Cl$ | 68.7 | 69 | 0 | 0 | 85.9 | 0 | 0 | 0 | 92.2 | 0 | 0 | 0 |
| | $CH_2Cl_2$ | 5.6 | 11 | 0 | 0 | 6.9 | 0 | 0 | 0 | 7.8 | 0 | 0 | 0 |
| | $CHCl_3$ | 0 | 0.4 | 0 | 0 | 0 | 0 | 0 | 0 | 0 | 0 | 0 | 0 |
| | $CO_2$ | 0 | 0 | 0 | 1 | 0 | 13.4 | 1.2 | 1.1 | 0 | 0.8 | 0.7 | 1 |
| | CO | 0 | 0 | 100 | 99 | 0 | 86.6 | 98.8 | 98.9 | 0 | 99.2 | 99.3 | 99 |
| | Coke | 25.7 | 19.6 | 0 | 0 | 7.2 | 0 | 0 | 0 | 0 | 0 | 0 | 0 |

From the experimental results, it could be confirmed that the optimal process temperature varied depending on the amount of palladium supported. In particular, when the amount of palladium supported was 4 wt % or 5 wt %, byproducts were rarely generated even at 480° C. which is a low temperature, unlike the case where the amount of palladium supported was 2 wt %. In particular, when the amount of palladium supported was 5 wt %, it could be confirmed that the selectivity of CO was close to about 100%. The result is because when the amount of palladium supported was 5 wt %, the number of active sites of the catalyst was sufficiently secured while palladium was uniformly dispersed on the surface of the carrier. The experimental results are illustrated in FIGS. 4 to 6.

The invention claimed is:

1. A partial oxidation process of hydrocarbons, comprising:
contacting inlet gas with a catalyst, said inlet gas comprising a hydrocarbon raw material gas and a hydrogen chloride gas,
wherein the catalyst comprises a catalyst material consisting of palladium (Pd), which catalyst material is supported on a carrier consisting of cerium oxide ($CeO_2$),
an amount of the catalyst material supported on the carrier is 2 wt % to 8 wt % based on a total weight of the catalyst,
the partial oxidation process is performed at a process temperature of 490° C. to 580° C., and
wherein the hydrocarbon raw material gas is converted to carbon monoxide, with no $CH_3Cl$, $CH_2Cl_2$ or $CHCl_3$ byproducts.

2. The partial oxidation process of claim 1, wherein a ratio of volume flow rates of the hydrocarbon raw material gas to the hydrogen chloride gas is 1:1 to 10:1.

3. The partial oxidation process of claim 1, wherein the inlet gas further comprises an oxygen gas, and a ratio of volume flow rates of the hydrocarbon raw material gas to the oxygen gas is 1:1 to 10:1.

4. The partial oxidation process of claim 1, wherein the partial oxidation process is performed at a pressure of 0.5 atm to 3 atm.

5. The partial oxidation process of claim 1, wherein a space velocity of the inlet gas is 10,000 ml/(h·gcat) to 50,000 ml/(h·gcat).

6. The partial oxidation process of claim 1, wherein the inlet gas further comprises at least one inert gas selected from the group consisting of nitrogen gas, helium gas, argon gas, and carbon dioxide gas.

7. The partial oxidation process of claim 6, wherein a ratio of volume flow rates of the hydrocarbon raw material gas to the at least one inert gas is 1:1 to 1:5.

8. The partial oxidation process of claim 1, wherein the catalyst is in a form of particles having an average particle diameter of 0.1 mm to 10 mm.

9. The partial oxidation process of claim 1, wherein said contacting is carried out by injecting the inlet gas into a reactor containing the catalyst, and wherein the reactor is a packed bed reactor, a fluidized bed reactor, or a circulating fluidized bed reactor.

10. The partial oxidation process of claim 9, wherein the hydrogen chloride gas is continuously injected into the reactor.

11. The partial oxidation process of claim 1, wherein the partial oxidation process is performed at a process temperature of 500° C. to 550° C.

12. The partial oxidation process of claim 1, wherein the partial oxidation process provides CO as a target product at a selectivity of 98% or more.

13. The partial oxidation process of claim 1, wherein the partial oxidation process provides CO as a target product at a selectivity of 99% or more.

* * * * *